US008263415B2

(12) United States Patent
Berling et al.

(10) Patent No.: US 8,263,415 B2
(45) Date of Patent: Sep. 11, 2012

(54) METHOD OF DETERMINING ANALYTE CONCENTRATION

(75) Inventors: Henrik Berling, Uppsala (SE); Tanja Jarhede, Storvreta (SE); Anita Larsson, Uppsala (SE); Hakan Roos, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 589 days.

(21) Appl. No.: 12/377,021

(22) PCT Filed: Sep. 12, 2007

(86) PCT No.: PCT/SE2007/000792
§ 371 (c)(1),
(2), (4) Date: Feb. 10, 2009

(87) PCT Pub. No.: WO2008/033073
PCT Pub. Date: Mar. 20, 2008

(65) Prior Publication Data
US 2010/0167422 A1 Jul. 1, 2010

Related U.S. Application Data

(60) Provisional application No. 60/825,664, filed on Sep. 14, 2006.

(30) Foreign Application Priority Data

Sep. 14, 2006 (SE) ........................................ 0601891

(51) Int. Cl.
*G01N 33/566* (2006.01)
(52) U.S. Cl. ......... 436/501; 435/7.1; 435/7.92; 436/518
(58) Field of Classification Search .................... None
See application file for complete search history.

(56) References Cited

U.S. PATENT DOCUMENTS

| 4,292,296 | A | * | 9/1981 | Parsons, Jr. ............... 436/500 |
| 4,459,359 | A | | 7/1984 | Neurath |
| 4,703,001 | A | | 10/1987 | Vodian et al. |
| 5,219,730 | A | | 6/1993 | Potocnjak et al. |
| 5,242,828 | A | | 9/1993 | Bergstrom et al. |
| 5,256,541 | A | | 10/1993 | Pouletty et al. |
| 5,313,264 | A | | 5/1994 | Ivarsson et al. |
| 5,382,530 | A | * | 1/1995 | Romelli et al. ............. 436/500 |
| 5,436,161 | A | | 7/1995 | Bergstrom et al. |
| 5,492,840 | A | | 2/1996 | Malmqvist et al. |
| 7,582,487 | B2 | * | 9/2009 | Malmqvist et al. ........... 436/165 |
| 2003/0003503 | A1 | | 1/2003 | Tsai et al. |
| 2009/0215200 | A1 | * | 8/2009 | Kahma ........................ 436/517 |

FOREIGN PATENT DOCUMENTS

| EP | 0 375 439 | 6/1990 |
| EP | 0 440 044 | 8/1991 |

OTHER PUBLICATIONS

Moxness et al., Immunogenicity Testing for Antibodies Directed Against Therapeutic Human Monoclonal Antibodies Using Electrochemiluminescent Detection, Abstract 59 Poster, 37th annual Oak Ridge Conference, Apr. 14-15, 2005, Baltimore MD.*
Friguet et al., Measurements of the True Affinity Constant in Solution of antigen-Antibody Complexes by Enzyme-Linked Immunosorbent Assay, Journal of Immunological Methods, 77 (1985) pp. 305-319.*
Cheung, C. Y., et al., Clinical Chemistry, 44(2), 299-303 (1998).
Li, Q., et al., BMC Neuroscience, 5(1), 21-27 (2004).
Moxness, M., et al., Clinical Chemistry, 51(10), 1983-1985 (2005).
Nishanian, P., et al., Journal of Infectious Diseases, 162(1), 21-28 (1990).
Saxena, U., et al., Journal of Clinical Laboratory Analysis, 6(4), 194-200 (1992).
Seiji, K., et al., Journal of Virological Methods, 22(2-3), 125-131 (1988).
Von Sydow, M., et al., British Medical Journal (Clinical Research Edition), 296(6617), 238-240 (1988).
Moxness, M., et al., "Immunogenicity Testing by Electrochemiluminescent Detection for Antibodies Directed against Therapeutic Human Monoclonal Antibodies", Clinical Chemistry, 2005, vol. 51, No. 10, p. 1983-1985.
Tomimori-Yamashita, J., et al., "Antibody-based enzyme-linked immunosorbent assay for determination of anti-PGL-I specific circulating immune complex in leprosy patients", Leprosy Review, vol. 70, No. 3, Sep. 1999, p. 261-271.
Nedelkov, D., et al., "Detection of bound and free IGF-1 and IGF-2 in human plasma via biomolecular interaction analysis mass spectrometry", FEBS Letters, 2003, vol. 536, p. 130-134.
Balk, S., et al., "Biology of Prostate-Specific Antigen", Journal of Clinical Oncology, vol. 21, No. 2, Jan. 2003, p. 383-391.
Patent Abstracts of Japan: 07-140144. Jun. 2, 1995.
Patent Abstracts of Japan: 2006-078364. Mar. 23, 2006.

* cited by examiner

Primary Examiner — Gary W Counts

(57) ABSTRACT

A method of determining the total concentration of an analyte in a fluid sample, wherein at least part of the analyte is present as a complex with an analyte-binding species. The methods includes the steps of:
a) subjecting the sample to conditions that reduce the binding affinity between analyte and analyte-binding species sufficiently to dissociate substantially any analyte complex and provide substantially all analyte in free form,
b) subjecting the sample to conditions that restore the binding affinity between analyte and analyte-binding species, and
c) immediately after the binding affinity has been restored, and before any substantial re-complexing of the analyte has taken place, determining the concentration of free analyte in the sample. A method of determining the concentration of complex-bound analyte in a sample is also disclosed.

13 Claims, 3 Drawing Sheets

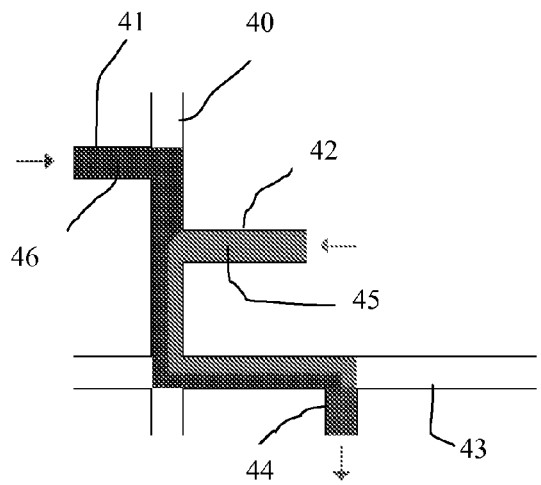
FIG. 3
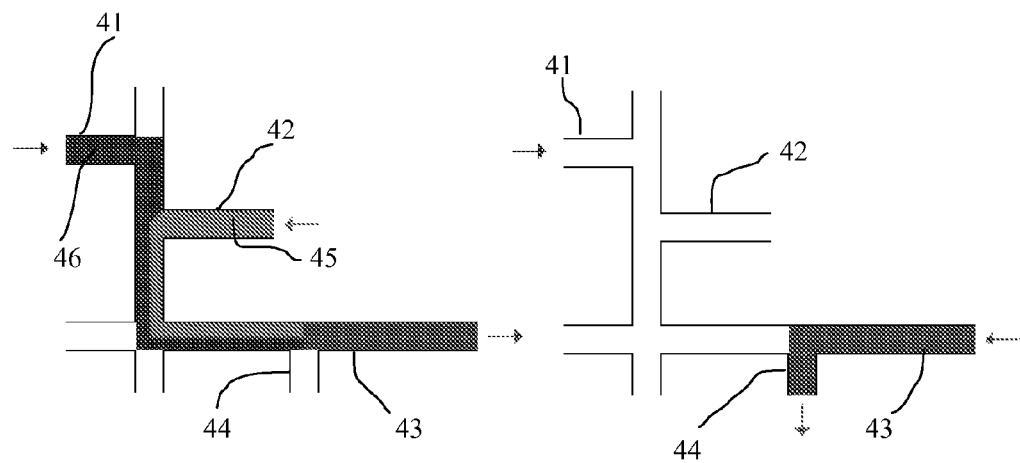
FIG. 4A  FIG. 4B

METHOD OF DETERMINING ANALYTE CONCENTRATION

CROSS-REFERENCE TO RELATED APPLICATIONS

This application is a filing under 35 U.S.C. §371 and claims priority to international patent application number PCT/SE2007/000792 filed Sep. 12, 2007, published on Mar. 20, 2008, as WO 2008/033073, which claims priority to patent application number 0601891-5 filed in Sweden on Sep. 14, 2006 and U.S. provisional patent application No. 60/825,664 filed Sep. 14, 2006.

FIELD OF THE INVENTION

The present invention relates to a method of determining the total concentration of analyte in fluid samples wherein the analyte at least partially may be present in complex form, typically as an immune complex. The invention also relates to a method of determining in such a fluid sample how the total analyte concentration is distributed between free and complex-bound analyte.

BACKGROUND OF THE INVENTION

Immunogenicity is the ability to, or the degree to which a particular substance may provoke an immune response, such as the production of antibodies. In immunogenicity studies, there is an increasing interest to measure and quantify the components "hidden" in immune complexes. For example, in the study of protein drugs, such as therapeutic antibodies, it is of interest to detect antibodies elicited against the drug. However, since the drug may be present in rather high concentrations in sera, the anti-drug antibodies may form immune complexes with the drug to a large extent. In the case of immunotherapeutic proteins used to elicit an immune reaction against a specific disease-causing protein, the situation is the opposite. The antibodies are in a great excess relative to the antigen, and it is of interest to know how much antigen that is complex-bound, since high levels of immune complexes may start complex activation. There are, however, today no convenient and efficient techniques for measuring the total concentration of free and complex-bound analyte in a serum sample, or how much analyte that is in free and complex form, respectively.

Moxness, M. S., et al., "Immunogenicity Testing for Antibodies Directed Against Therapeutic Human Monoclonal Antibodies Using Electrochemiluminescent Detection", Abstract 59 and Poster, 37$^{th}$ Annual Oak Ridge Conference, April 14 & 15, 2005, Baltimore, Md., disclose an assay for monitoring immune response against human therapeutic monoclonal antibodies (drugs). A rabbit polyclonal antibody specific for each drug was used as surrogate analyte and added to serum. Drug was then added, and the serum was treated with acid (pH 3.3) for one hour to dissociate analyte-drug complexes, brought to neutral pH and assayed. In the assay, the neutralized serum sample was incubated over night with (i) drug conjugated with a ruthenium complex that emits light through electroluminescence (ECL), and (ii) drug conjugated with biotin. The mixture was then transferred to streptavidin-coated plates equipped with electrodes to capture biotin-drug/analyte-ruthenium drug complexes, and ECL signals were measured on an ECL-analyzer and normalized against a negative control in every assay. However, all complex-bound analytes can not be measured since analyte complexed with biotin-drug conjugate at both binding sites, or ruthenium-drug conjugate at both binding sites will not be detected, and a determination of the total analyte concentration can therefore not be obtained.

Tomimori-Yamashita, J., et al., *Lepr. Rev.* (1999) 70: 261-271 discloses determination of anti-PGL-I specific circulating immune complex in leprosy patients. The circulating immune complexes in sera were precipitated by adding polyethylene glycol and isolate the precipitate by centrifugation. After dissolving the precipitate in EDTA, the solution was acidified with HCl-glycine and then neutralized with potassium hydrogenphosphate. The levels of IgG or IgM antibodies against PGL-I were then tested by ELISA within 30 minutes by incubating the solution in PGL-I coated wells for 90 to 180 minutes, reacting with enzyme conjugate and substrate, and spectrophotometrically reading the color developed through the enzyme activity. However, as is well known in the art, PEG does not precipitate all complexed analytes, and a determination of the total analyte concentration will therefore not be obtained Both the above described prior art methods require lengthy incubations and are therefore not suited for flow cell assay formats. There is therefore a need for a quick and easy-to-perform assay that permits determination of free as well as any complexed analyte, which is capable of detecting all complexed analytes and which also is well suited for flow cell applications.

SUMMARY OF THE INVENTION

The above and other objects and advantages are provided by a method for determining the total concentration of free and complexed analyte wherein a sample is first treated to disrupt any analyte complex so that all analyte is in free form. The sample is then treated to permit re-complexing of the analyte simultaneously as the concentration of free analyte in the sample is determined before re-complexing of the free analyte can occur to any substantial extent. The determined concentration of free analyte will therefore be representative of the total concentration of analyte in the sample.

In one aspect, the present invention provides a method of determining the total concentration of an analyte in a fluid sample, wherein at least part of the analyte is present as a complex with an analyte-binding species, comprising the steps of:
a) subjecting the sample to conditions that reduce the binding affinity between analyte and analyte-binding species sufficiently to dissociate substantially any analyte complex and provide substantially all analyte in free form,
b) subjecting the sample to conditions that restore the binding affinity between analyte and analyte-binding species, and
c) immediately after the binding affinity has been restored, and before any substantial re-complexing of the analyte has taken place, determining the concentration of free analyte in the sample.

In a preferred embodiment, the determination of free analyte comprises contacting the sample with a solid support surface having an analyte-binding ligand immobilized thereon to bind analyte to the ligand.

In another aspect, the present invention provides a method of determining the concentration of complex-bound analyte in a sample which comprises the steps of:
a) determining the total concentration of analyte in a sample according the method aspect above; and
b) determining the concentration of free analyte in the sample, the difference between the concentrations obtained in steps a) and b) representing the concentration of complex-bound analyte.

In still another aspect, the present invention provides a method of determining the capability of an analyte to form a complex with one or more species in a sample containing the analyte, which comprises the steps of:

a) subjecting the sample to conditions that reduce the binding affinity between analyte and analyte-binding species sufficiently to dissociate substantially any analyte complex and provide substantially all analyte in free form, b) subjecting the sample to conditions that restore the binding affinity between analyte and analyte-binding species, c) immediately after the binding affinity has been restored, and before any substantial re-complexing of the analyte has taken place, contacting the sample with a solid support having the analyte immobilized thereon, and d) analyzing the species bound to the immobilized analyte.

A more complete understanding of the present invention, as well as further features and advantages thereof, will be obtained by reference to the following detailed description and drawings.

BRIEF DESCRIPTION OF THE DRAWINGS

FIG. 3 is a schematic partial view of a microfluidic system illustrating one variant of mixing two fluids therein.

FIGS. 4A and 4B schematic partial view of a microfluidic system illustrating another variant of mixing two fluids therein.

DETAILED DESCRIPTION OF THE INVENTION

Figure 1:
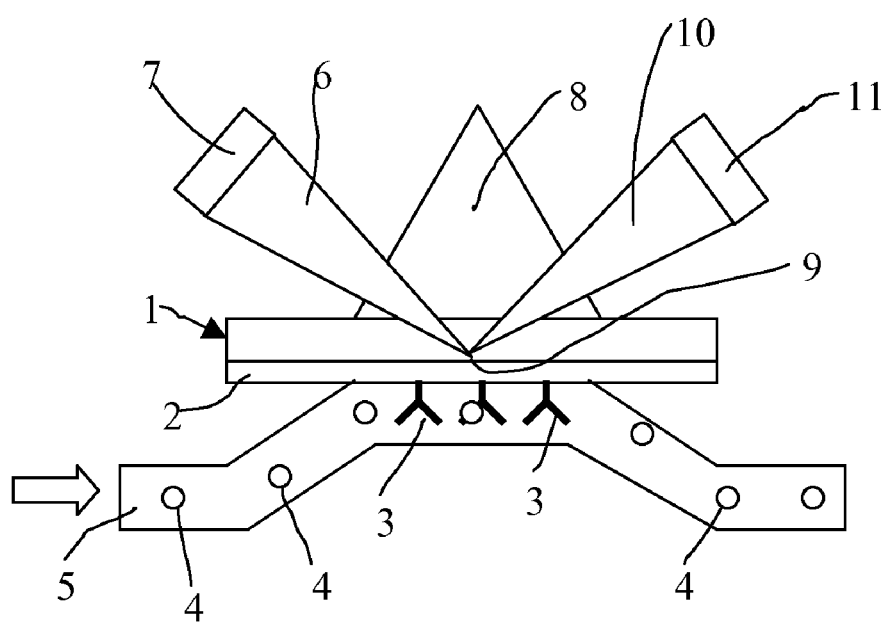
FIG. 1 is a schematic side-view of biosensor system based on surface plasmon resonance (SPR).

As mentioned above, the present invention relates to a method of determining the total concentration of analyte in fluid samples wherein the analyte at least partially may be present as a complex(es) with an analyte-binding species, typically as an immune complex.

According to the invention, the sample is first subjected to conditions that dissociate any complexes present in the sample (by reducing the affinity for the binding between the analyte and analyte-binding species), typically by adding a dissociating agent to the sample, so that all analyte will be in free form. The sample is then subjected to conditions that restore the binding affinity, and the concentration of free analyte in the sample is determined substantially immediately before any substantial re-complexing of the analyte has taken place, preferably via its binding to an anlyte-specific ligand.

The sample may be any sample that contains or is suspected of containing an analyte of interest which at least partially is in complex form. Typically, however, the sample is a serum or plasma sample from a mammal, preferably human, and the complex is an immune complex (i.e. an antigen-antibody complex).

The analyte may, for example, be an antibody elicited in response to a drug, e.g. a protein drug, such as a therapeutic antibody.

The term "antibody" as used herein refers to an immunoglobulin which may be natural or partly or wholly synthetically produced and also includes active fragments, including Fab antigen-binding fragments, univalent fragments and bivalent fragments. The term also covers any protein having a binding domain which is homologous to an immunoglobulin binding domain. Such proteins can be derived from natural sources, or partly or wholly synthetically produced. Exemplary antibodies are the immunoglobulin isotypes and the Fab, Fab', F(ab')$_2$, scFv, Fv, dAb, and Fd fragments.

Examples of other analyte-complexes (usually protein-complexes) that may need to be dissociated to permit measuring the analyte include PSA (prostate specific antigen), PSA being a protein which to a great extent is in complex-form and for which it is of interest to be able to determine the proportion of complex. In blood, about 70-90% of the PSA is in complex with alpha-1-antichymotrypsin, but PSA is also known to form complexes with e.g. protein C inhibitor, alpha-1-antitrypsin and alpha-2-macroglobulin. The ratio of free to total PCA would be a useful marker for prostate cancer, but there is presently no antibody that could be used to detect complexes with alpha-2-macroglobulin, PSA being completely enclosed by alpha-2-macroglobulin in the complex (Balk et al. (2003) J. Clin. Oncology 21, 383-391). This would presumably be the case also for other protein complexes.

A variety of reagents and conditions may be used to accomplish dissociation of analyte-containing complexes. Immune complexes may, for example, be dissociated by acidic or basic agents which subject the complex to low or high pH conditions, respectively. Restoration of analyte binding activity may then be effected by bringing the acidified or alkalized sample to a substantially neutral pH. Other reagents and conditions include, for example, chaotropic salts, high or low ionic strength, organic salts.

A basic feature of the invention is that the measurement of analyte concentration takes place substantially immediately after the sample has been treated to restore the binding capability (to ligand as well as to complexing species), such as by neutralization of an acidified or alkalized sample. By "substantially immediately" is meant that re-complexing of the analyte (depending on inter alia the analyte, the complexing species and the assay device used) should not have had time to take place to any appreciable extent. On the other hand, sufficient time must be provided for the treatment of the sample to restore the analyte binding capability, such as neutralization, to be substantially completed, before the measurement takes place (which depends on inter alia the reagents and assay device used). It is, however, within the competence of a person skilled in the art to find an optimum time for the measurement for each particular assay system. Preferably, no more than about 5% of the analyte should be in complex form, more preferably less than about 1%, when the analyte concentration is measured.

By also determining the analyte concentration without complex dissociation, the proportion of free analyte to complex-bound analyte in the sample may be determined.

Preferably, a heterogeneous assay system comprising a solid support surface with an immobilized analyte-specific ligand is used for measuring the analyte concentration by detecting directly or indirectly the amount of binding to the solid support surface, either of the analyte (direct assay, including sandwich assay; or displacement assay) or of a detectable analyte analogue (competition assay).

The solid support surface may have a variety of shapes as is per se known in the art, but typically comprises a surface area of a cuvette or well, such as a micro-well or, preferably, a flow cell.

In case the analyte is an antibody, the immobilized ligand may be an antigen. When, on the other hand, the analyte is e.g. PSA, the solid support surface may have e.g. anti-PSA and preferably also alpha-1-antichymotrypsin, protein C inhibitor, alpha-1-antitrypsin and alpha-2-macroglobulin immobilized thereto.

A heterogeneous assay based on the inventive concept could also be used in so-called ligand fishing. Assume, for example, that it is of interest to know which species, such as proteins, that bind in vivo to a specific protein. The specific protein may then be immobilized to a solid support surface, and the sample (e.g. a cell extract or plasma) containing the specific protein is contacted with the surface immediately after the surface has been treated to first dissociate complexes and then restore the binding affinity of the interacting species. (Without such treatment of the sample, if all or substantially all binding proteins would already be bound to the specific protein in the sample, no or very little binding of binding proteins to the surface would be obtained). The protein or proteins that have bound to the specific protein immobilized on the surface may then be identified, such as by mass spectrometry.

As mentioned above, it is important that the sample is contacted with the solid support surface, or detection area, substantially immediately after the sample has been treated to restore the binding capability of the analyte. In the case of a flow cell, the latter may therefore comprise an inlet which via a junction is connected to first and second conduits. Sample containing dissociated complex may be introduced into the first conduit, and a fluid containing an agent for restoring the binding capability of the analyte into the second conduit, so that the two fluids mix at the junction of the flow cell inlet conduit and the mixed fluids pass through the flow cell over the solid support area.

The distance between the detection area and the junction, and the fluid flow rates in the first and second conduits should be selected such that when the mixed fluids reach the solid support area, the binding capability of the analyte has substantially been restored, e.g. an acidified sample is substantially neutralized by an alkaline fluid, but re-complexing of the analyte has substantially not taken place.

Optionally, mixing may be improved by, e.g., directing the fluid mixture into a side channel or loop before redirecting the mixture into the flow cell, or by other means.

The detection system used for measuring analyte concentration may be based on use of a label or may, preferably, be label-free. Preferably, detection is performed with a sensor, such as a biosensor, in which case the solid support surface is a sensing surface of the (bio)sensor.

A biosensor is broadly defined as a device that uses a component for molecular recognition (for example a layer with immobilised antibodies) in either direct conjunction with a solid state physicochemical transducer, or with a mobile carrier bead/particle being in conjunction with the transducer. While such sensors are typically based on label-free techniques detecting a change in mass, refractive index or thickness for the immobilized layer, there are also biosensors relying on some kind of labelling. Typical sensors for the purposes of the present invention include, but are not limited to, mass detection methods, such as optical methods and piezoelectric or acoustic wave methods, including e.g. surface acoustic wave (SAW) and quartz crystal microbalance (QCM) methods. Representative optical detection methods include those that detect mass surface concentration, such as reflection-optical methods, including both external and internal reflection methods, which may be angle, wavelength, polarization, or phase resolved, for example evanescent wave ellipsometry and evanescent wave spectroscopy (EWS, or Internal Reflection Spectroscopy), both of which may include evanescent field enhancement via surface plasmon resonance (SPR), Brewster angle refractometry, critical angle refractometry, frustrated total reflection (FTR), scattered total internal reflection (STIR) (which may include scatter enhancing labels), optical wave guide sensors, external reflection imaging, evanescent wave-based imaging such as critical angle resolved imaging, Brewster angle resolved imaging, SPR-angle resolved imaging, and the like. Further, photometric and imaging/microscopy methods, "per se" or combined with reflection methods, based on for example surface enhanced Raman spectroscopy (SERS), surface enhanced resonance Raman spectroscopy (SERRS), evanescent wave fluorescence (TIRF) and phosphorescence may be mentioned, as well as waveguide interferometers, waveguide leaking mode spectroscopy, reflective interference spectroscopy (RIfS), transmission interferometry, holographic spectroscopy, and atomic force microscopy (AFR).

Biosensor systems based on SPR and other detection techniques are commercially available today. Exemplary such SPR-biosensors include the above-mentioned BIACORE® instruments. A detailed discussion of the technical aspects of the BIACORE® instruments and the phenomenon of SPR may be found in U.S. Pat. No. 5,313,264. More detailed information on matrix coatings for biosensor sensing surfaces is given in, for example, U.S. Pat. Nos. 5,242,828 and 5,436,161. In addition, a detailed discussion of the technical aspects of the biosensor chips used in connection with the BIACORE® instrument may be found in U.S. Pat. No. 5,492,840. The full disclosures of the above-mentioned U.S. patents are incorporated by reference herein.

Figure 2:
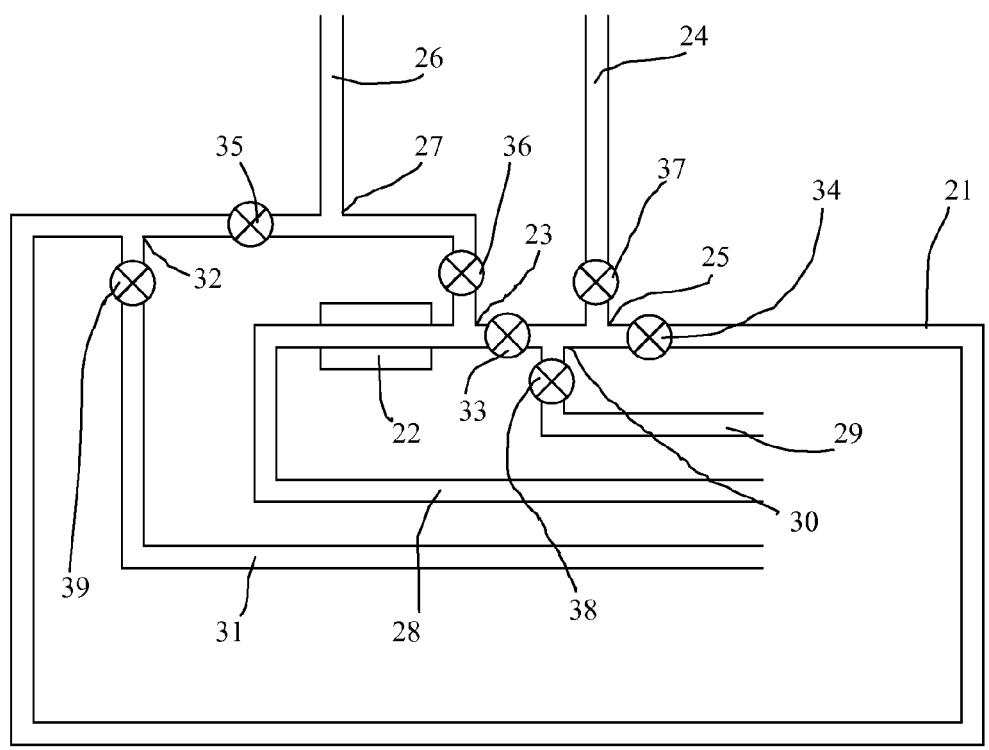
FIG. 2 is schematic partial illustration of the flowpaths in an integrated microfluidic cartridge of a commercial biosensor instrument.

With reference to FIGS. 1 and 2, it will now, for illustrative purposes only, briefly be described how the invention may be performed with a BIACORE® or analogous biosensor system.

The processing unit of a BIACORE® instruments typically comprises two liquid delivery pumps, one for maintaining a constant flow of liquid over a sensor chip surface and the other for handling samples, an autosampler, an integrated microfluidic cartridge (IFC), containing liquid delivery channels, sample loop and valves, a detector unit, including optical and electronic components for creating and measuring SPR response, four detector flow cells formed by the IFC pressing against the sensor chip, and microprocessors for controlling pumps, autosampler and IFC valves, and for basic processing of the SPR signal.

A schematic illustration of the detection system is shown in FIG. 1. Sensor chip 1 has a gold film 2 supporting capturing molecules 3 (ligands), e.g. antibodies, exposed to a sample flow with analytes 4, e.g. an antigen, through a flow channel 5. Together with sensor chip 1 the flow channel defines a "flow cell", the gold film with antibodies forming a "sensing surface". Monochromatic p-polarised light 6 from a light source 7 is coupled by a prism 8 to the glass/metal interface 9 where the light is totally reflected. The intensity of the reflected light beam 10 is detected by an optical detection unit 11 (photodetector array).

When molecules in the sample bind to the capturing molecules on the sensor chip surface, the concentration, and therefore the refractive index at the surface changes and an SPR response is detected. Plotting the response against time during the course of an interaction will provide a quantitative measure of the progress of the interaction. Such a plot is usually called a sensorgram. In the BIACORE® systems, the SPR response values are expressed in resonance units (RU). One RU represents a change of 0.0001° in the angle of minimum reflected light intensity, which for most proteins is roughly equivalent to a change in concentration of about 1 $pg/mm^2$ on the sensor surface.

The delivery of liquid to the sensor chip is controlled by the above-mentioned IFC which consists of a series of channels and pneumatic valves encased in a plastic housing. Samples are injected from the autosampler into the IFC, which connects directly with the detector flow cells.

FIG. 2 is a schematic illustration of the flow cell and sample loop part of a BIACORE® 3000 instrument, which is similar to the IFC of the BIACORE® T100 used in the Examples below.

In FIG. 2, a channel 21, referred to below as loop channel, extends in a loop fashion between the inlet end of a flow cell 22 (for clarity, only one of the four flow cells is shown) and a junction 23 on channel 21 close to the flow cell. In a typical IFC, the loop channel has a capacity of about 100 µl. An inlet channel 24 for sample (autosampler inlet) connects to channel 21 at a junction 25 further away from the flow cell inlet. An inlet channel 26 for continuous liquid flow (buffer) is connected to the loop end part of channel 21 at a junction 27. The outlet end of the flow cell 22 opens in a first waste channel 28. A second waste channel 29 extends from a junction 30 on channel 21 between junctions 23 and 25. A third waste channel 31 is attached to channel 21 at a junction 32. Pneumatic valves 33-36 are provided on channel 21, a valve 37 is provided on sample inlet channel 24, and valves 38 and 39 are provided on waste channels 29 and 31, respectively. The valves are operated by a compressed air system (not shown). The part of channel 21 that extends between junctions 25 and 32 may be used as a "sample loop" for loading sample as will be described below. The inlet channels 24 and 26 as well as waste channels 28, 29 and 31 extend to a remote end (with regard to the flow cell 22) of the IFC where they connect to a connector block (not shown) which has two inlet ports for buffer flow and sample/reagents (autosampler needle port), respectively.

Sample injection may be performed in two operation modes, "direct injection" and "loop injection" by proper control of the valves and pumps.

In direct injection, valves 34, 36 and 38 are closed and the remaining valves are open. Sample is pumped directly into the flow cell 22 via sample inlet channel 24 and the portion of loop channel 21 that extends between junction 25 and the flow cell 22.

In loop injection, on the other hand, valves 33, 35 and 38 are first closed and the remaining valves open, and sample is loaded via sample inlet channel 24 into loop channel 21, while a constant flow of buffer is pumped through the flow cell 22 via inlet channel 26. Valves 33 and 35 are then opened while valves 36, 37 and 39 are closed, and buffer is pumped through inlet channel 26 into loop channel 21 to push the loaded sample volume in the opposite direction from loading out of the sample loop into the flow cell 22.

Assume now that an antibody in a sample is to be detected where the sample contains an antigen that forms an antigen-antibody complex with the antibody, at least a part of the target antibody therefore being in complex form. To perform the method of the present invention, the sensing surface of the flow cell 22 in FIG. 2 supports the antigen. The sample is first acidified to dissociate the antigen-antibody complexes, then the acidified sample solution is neutralized to restore the binding capability of the antibody, and the neutralized sample solution containing free antibody is flowed trough the flow cell to permit antibody to bind to the immobilized antigen on the sensing surface. To ensure that re-formation of antigen-antibody complexes has not taken place to any substantial extent before the neutralizing solution reaches the flow cell sensing surface, the mixing of the acidified sample with the neutralizing solution should, as mentioned above, take place close to the flow cell inlet. Mixing the solutions outside the BIACORE® instrument and injecting the neutralized sample in, for example, the direct injection mode described above has been demonstrated to allow too extensive re-complexing in the sample before the latter reaches the flow cell. Therefore, a modified injection mode was developed.

In this mode, referring to FIG. 2, the neutralizing solution is introduced via the sample inlet 24 and loaded in the sample loop 21 in the same way as for the loading of sample described above, i.e. with valves 33, 35 and 38 closed and the remaining valves open. Buffer flow though inlet 26 is then used to inject the neutralizing solution into the flow cell 22 as described above, i.e. by opening valves 33 and 35 and closing valves 36 and 39, and pumping buffer via inlet channel 26 into loop channel 21, simultaneously as acidified sample solution is supplied through the sample inlet 24. The acidified sample solution and the neutralizing solution will thereby meet and start mixing at junction 25. The proportions of acidified sample solution and neutralizing solution may be varied by varying the flow rate ratio of the fluid flows through sample inlet 24 and inlet 26.

Alternatively, the sample solution may, of course, be loaded in the sample loop and the neutralizing solution supplied though the sample inlet 24.

A more detailed representation of how mixing of the two fluids may take place is schematically illustrated in FIGS. 3, 4A and 4B, each of which show a portion of a micro-fluidic system comprising a first channel 40 with side channels 41 and 42, and a crossing channel 43 which has a side channel 44. Valves (not shown) are provided to control the passage of a pumped fluid or fluids through the channel system.

FIG. 3 shows a mixing variant corresponding to that described in connection with FIG. 2 above where the two solutions are mixed and then directly led to the flow cell(s). Acidified sample solution 45 is introduced through side channel 42, and neutralizing solution 46 through side channel 41, or vice versa. The two solutions are then mixed on their way to the flow cell (not shown) via channel 44.

An alternative mixing variant is shown in FIGS. 4A and 4B where the solution mixture is first led into a side channel (or loop) before being redirected to the flow cell. Acidified sample solution 45 and neutralizing solution 46 are introduced through side channels 42 and 41, respectively. The mixing solutions 45 and 46 are then, however, in a first step (FIG. 4A) not led directly through side channel 44 to the flow cell as in FIG. 3, but are allowed to flow further in channel 43 past the side channel junction. The flow is then stopped and reversed to pump the mixed fluid volume through side channel 44 to the flow cell (FIG. 4B). This is done repeatedly with small fluid volumes each time so that the two solutions will not be mixed for too long a time (to prevent re-complexing), i.e. a plurality of pulses rather than a long injection of mixed fluid will be passed to the flow cell. In comparison with the variant in FIG. 3, the mixing procedure in FIGS. 4A and 4B may ensure a better mixing of the two solutions with each other, which in turn reduces non-specific binding to the sensor chip.

There are, of course a number of other ways of improving mixing in the micro-fluidic system. These include, for example, on the one hand, designing the channel system to include stationary constrictions, bends etc which break up the laminar flow or, on the other hand, using active mixers. In the latter case a membrane, such as, e.g., the valve membranes present in the micro-fluidic systems of the above-mentioned BIACORE® 3000 and BIACORE® T100 instruments, may be used as an actuator by vibrating to create stirring which breaks up the laminar flow. Alternatively, one or both fluid flows may be pulsating so that sample and neutralizing buffer are segmented, preferably into very small segments. Still other alternatives include using alternating valves which micro-segment the flow, micro-propellers, unstable flaps, magnetic stirrers, magnetic beads etc. Instead of active mixers, it would also be possible to use an external field, such as an ultrasound field or an electric field, to speed up mixing.

In the following Examples, various aspects of the present invention are disclosed more specifically for purposes of illustration and not limitation.

EXAMPLES

Instrumentation

A BIACORE® T100 (Biacore AB, Uppsala, Sweden) was used. This instrument, which is based on surface plasmon resonance (SPR) detection at a gold surface on a sensor chip, uses a micro-fluidic system (integrated micro-fluidic cartridge—IFC) for passing samples and running buffer through four individually detected flow cells, designated Fc 1 to Fc 4, one by one or in series. The IFC is pressed into contact with the sensor chip by a docking mechanism within the BIACORE® T100 instrument.

As sensor chip was used Series CM5 (Biacore AB, Uppsala, Sweden) which has a gold-coated (about 50 nm) surface with a covalently linked hydrogel matrix (about 100 nm) of carboxymethyl-modified dextran polymer.

The output from the instrument is a "sensorgram" which is a plot of detector response (measured in "resonance units", RU) as a function of time. An increase of 1000 RU corresponds to an increase of mass on the sensor surface of approximately 1 ng/mm$^2$.

In the Examples below, analyses were performed with the flow cells Fc 1 to Fc 4 coupled in series. A "prototype inject" was used which mixes two solutions adjacent to the flow cells of the IFC during the injection over the flow cells in a similar manner as described above with reference to FIG. 2.

As running buffer was used HBS-EP+(0.01 mM HEPES, 0.15 M NaCl, 3 mM EDTA and 0.05% v/v Surfactant P20, pH 7.4) (Biacore AB). Unless indicated otherwise, the flow rate was 5 µl/min for sample and 30 µl/min for neutralizing solution, and the temperature was 25° C.

Example 1

Measurement in Buffer of Small Amounts of Anti-HSA Antibody in the Presence of High Concentrations of HSA Human serum albumin (Sigma-Aldrich, Missouri, USA) was diluted to 50 µg/ml in 10 mM acetate pH 5.0 and immobilized to flow cell 3 (Fc 3) in the BIACORE® T100 to about 9 kRU using standard amine coupling (Amine coupling kit, Biacore AB).

100 µl samples containing 110 µg/ml HSA (Sigma-Aldrich) and different concentrations of anti-HSA (in-house reagent) were prepared. As control was used a sample without HSA.

The samples were acidified with 50 µl of 0.2 M glycine pH 2.8.

Each sample was then injected into the BIACORE® T100, using the prototype inject to mix the sample with HBS-EP+ (0.1 M HEPES, 0.15 M NaCl, 3 mM EDTA and 0.05% v/v Surfactant P20, pH 7.4—Biacore AB) in the proportions 15:85, and thereby neutralize the sample, before serially passing all the flow cells of the IFC. Detection was performed in Fc 3 (previous experiments had indicated that the mixture of acidic sample and neutralizing solution was optimal in this flow cell; i.e. in Fc 1 and Fc 2, the neutralization of the sample was not complete, whereas in Fc 4, re-complexing had started). Regeneration of the HSA was performed with 10 mM glycine pH 2.0 (Biacore AB). The results are shown in Table I below.

TABLE I

| Anti-HSA (µg/ml) | HSA 0 µg/ml (RU) | HSA 110 µg/ml (RU) |
|---|---|---|
| 50 | 2785 | 2364 |
| 5 | 222 | 248 |
| 0.5 | 9 | 14 |
| 0.05 | −26 | −23 |

As shown in the table, 5 µg/ml anti-HSA may be detected in the presence of a 50 times molar excess of HSA.

Example 2

Measurement of Anti-Beta-2-Microglobulin in Buffer with and without Beta-2-Microglobulin 20 µg/ml beta-2-microglobulin (β2µ (in-house reagent) in 10 mM acetate pH 4.5 (Biacore AB) were immobilized to flow cell 3 (Fc 3) in the BIACORE® T100 to about 1.7 kRU using standard amine coupling (Amine coupling kit, Biacore AB).

100 µl buffer samples containing 100 µg/ml anti-beta-2-microglobulin (anti-β2µ) (in-house reagent) and different concentrations of beta-2-microglobulin (β2µ)(in-house reagent) in HBS-EP+(Biacore AB) were prepared. Buffer samples were then acidified by mixing with 50 µl of 0.2 M glycine, pH 2.8. Control samples were not acidified.

Each sample was then injected into the BIACORE® T100, using the prototype inject to mix the sample with HBS-EP+ (Biacore AB) in the proportions 15:85, and thereby neutralize the sample, before serially passing all the flow cells of the IFC. Regeneration was performed with glycine, pH 1.5 (Biacore AB). The results are shown in Table II below.

TABLE II

| β2µ (µg/ml) | Control sample (RU) | Acidified sample (RU) |
|---|---|---|
| 0 | 1445 | 1483 |
| 10 | 660 | 1316 |
| 50 | 17 | 1239 |

From the Table it is seen that for the acidified samples, approximately the same response levels were obtained, irrespectively of whether β2µ had been added or not (complexes between anti-β2µ and β2µ were disrupted), whereas for the control samples (not acidified) the response levels were drastically reduced when β2µ was present (complexing with anti-β2µ).

Example 3

Measurement of Anti-Beta-2-Microglobulin in Human Plasmas with and without Beta-2-Microglobulin 20 µg/ml β2µ (in-house reagent) in 10 mM acetate pH 4.5 (Biacore AB) were immobilized to flow cell 3 (Fc 3) in the BIACORE® T100 to about 1.7 kRU using standard amine coupling (Amine coupling kit, Biacore AB).

100 μl human plasma samples were prepared which contained either (i) 50 μg/ml anti-β2μ or (ii) 50 μg/ml anti-β2μ and 5 μg/ml β2μ, and 1% v/v Surfactant P20 (Biacore AB). (Human plasma samples usually contain about 1 μg/ml of β2μ.) The plasma samples were then acidified by mixing with 15 μl of 1 M HCl (gives pH 2-3).

Each sample was then injected into the BIACORE® T100, using the prototype inject to mix the sample with 0.1 M $K_2HPO_4$, pH 9.0, plus 1% v/v Surfactant P20 (Biacore AB) in the proportions 15:85, and thereby neutralize the sample, before serially passing all the flow cells of the IFC. Regeneration was performed with glycine pH 1.5 (Biacore AB). The results are shown in Table III below.

TABLE III

| Plasma No. | Acidified sample with anti-β2μ (RU) | Acidified sample with anti-β2μ plus β2μ (RU) |
|---|---|---|
| 1953 | 1465 | 1419 |
|  | 1460 | 1415 |
| 1954 | 1213 | 1182 |
|  | 1175 | 1179 |
| 1955 | 1142 | 1118 |
|  | 1117 | 1130 |
| 1956 | 1010 | 981 |
|  | 991 | 980 |
| 1957 | 1144 | 1118 |
|  | 1132 | 1120 |
| 1958 | 1172 | 1142 |
|  | 1164 | 1143 |
| 1961 | 884 | 866 |
|  | 879 | 878 |

As can be seen in the Table, the antibody response was substantially identical for each duplicate sample irrespectively of whether the antibody had been complexed with β2μ or not. The varying response levels between the plasma samples is due to the fact that the experiments had been run with different sensorchips on different occasions. This is demonstrated by Table IV below which shows the results obtained when three of the plasma samples were run as described above but on one and the same sensor chip surface at the same time. The plasma samples contained 100 μg/ml anti-β2μ and 1% v/v Surfactant P20. As control was used a buffer sample containing 100 μg/ml anti-β2μ (in-house reagent) and 1% v/v Surfactant P20 in HBS-EP+, pH 7.4.

TABLE IV

| Plasma No. | Acidified sample with anti-β2μ (RU) |
|---|---|
| 1953 | 2039 |
| 1958 | 1836 |
| 1961 | 1746 |
| 1958 | 1812 |
| 1953 | 1857 |
| Buffer | 1949 |

As appears from the table, there was a good concordance between the different plasma samples. The plasma sample values also corresponded well to the value for antibody in buffer.

It is to be understood that the invention is not limited to the particular embodiments of the invention described above, but the scope of the invention will be established by the appended claims.

The invention claimed is:

1. A method of determining the total concentration of an analyte in a fluid sample, wherein at least part of the analyte is present as a complex with an analyte-binding species, comprising the steps of:
    a) subjecting the sample to conditions that reduce the binding affinity between analyte and analyte-binding species sufficiently to dissociate substantially any analyte complex and provide substantially all analyte in free form,
    b) subjecting the sample to conditions that restore the binding affinity between analyte and analyte-binding species, and
    c) immediately after the binding affinity has been restored, and before any substantial re-complexing of the analyte has taken place, determining the concentration of free analyte in the sample, wherein the concentration determined corresponds to the total concentration of analyte in the sample.

2. The method of claim 1, wherein the determination of free analyte in the sample comprises contacting the sample with a solid support having an analyte-binding ligand immobilized thereon to bind analyte to the immobilized ligand.

3. The method of claim 1, wherein the conditions that reduce the binding affinity in step a) and restore the binding affinity in step b) comprise changing the pH-value of the sample.

4. The method of claim 1, wherein the complex is an acid-dissociable complex, step a) comprises acidifying the sample, and step b) comprises neutralizing the acidified sample.

5. The method of claim 1, wherein the complex is an immune-complex.

6. The method of claim 1, wherein the analyte is an antibody to a therapeutic antibody and the sample contains the therapeutic antibody.

7. The method of claim 1, wherein the concentration of the free analyte is determined by using a label-free detection technique.

8. The method of claim 7, wherein the label-free detection technique comprises evanescent wave sensing.

9. The method of claim 1, wherein at least step c) is performed in a flow cell.

10. The method of claim 9, wherein step b) is also performed in a flow cell, and the flow cell comprises a detection area with immobilized ligand, and an inlet which via a junction is connected to first and second conduits, further wherein step b) comprises flowing a sample with dissociated analyte complexes in the first conduit and a fluid capable of restoring the analyte binding capability in the second conduit so that the two fluids mix at the junction of the flow cell inlet conduit and the mixed fluids pass through the flow cell over the detection area.

11. The method of claim 10, wherein (i) the distance between the detection area and the junction, and (ii) the fluid flow rates in the first and second conduits are selected such that when the mixed fluids reach the detection area, the analyte binding capability is substantially restored but re-complexing of the analyte has substantially not taken place.

12. The method of claim 10, wherein the fluid flowing in the first conduit is an acidified sample, and the fluid flowing in the second conduit is an alkaline fluid.

13. The method of claim 12, wherein, when the mixed fluids reach the detection area, the acidified sample is substantially neutralized but re-complexing of the analyte has substantially not taken place.

* * * * *